United States Patent [19]

Kassis

[11] Patent Number: 5,681,708

[45] Date of Patent: Oct. 28, 1997

[54] METHOD FOR SCREENING COMPOSITIONS

[75] Inventor: Shouki Kassis, Audubon, Pa.

[73] Assignee: SmithKline Beecham Corporation, Philadelphia, Pa.

[21] Appl. No.: 321,709

[22] Filed: Oct. 12, 1994

[51] Int. Cl.$^6$ .................................................. G01N 33/53
[52] U.S. Cl. .................... 435/724; 435/7.1; 435/7.8; 435/7.93; 436/518
[58] Field of Search ..................... 435/7.1, 7.2, 7.4, 435/7.24, 7.5; 436/517, 518, 536

[56] References Cited

FOREIGN PATENT DOCUMENTS

WO 93/23559  11/1993  WIPO.

OTHER PUBLICATIONS

Yoshida et al: Biochemi. Biophys. Acta, vol. 1137, 1992, pp. 321–330.
Weiss et al., Ann. Rev. Immuno. 4, 593–619 (1986).
Rudd et al., Immunol. Rev. 111, 225–266 (1989).
Bierer et al., Ann. Rev. Immunol. 7, 579–599 (1989).
Bierer et al., Immunol. Rev. 111, 267–294 (1989).
Eichmann et al., Eur. J. Immunol. 17, 643–650 (1987).
Anderson et al., J. Immunol. 139, 678–682 (1987).
Reinherz et al., Immunol. Rev. 81, 95–129 (1985).
Snow et al., J. Biol. Chem. 258, 14675–14681 (1983).
Rudd et al., Proc. Natl. Acad. Sci. USA, 85, 5190–5194 (1988).
Veillette et al., Cell, 55, 301–308 (1988).
Straus et al., Cell, 70, 585–593 (1992).
Chan et al., Ann. Rev. Immunol. 12, 555–592 (1994).
Molina et al., Nature, 357, 161–164 (1992).
Veillette et al., Nature, 338, 257–259 (1989).
Miceli et al., Proc. Natl. Acad. Sci. USA, 88, 2623–2627 (1991).
Glaichenhaus et al., Cell, 64, 511–520 (1991).
Turner et al., Cell, 60, 755–765 (1990).
Berlinck et al., Tetrahedron Letters 31, 6531–6534 (1990).

*Primary Examiner*—Ponnathapura Achutamurthy
*Attorney, Agent, or Firm*—Kirk Baumeister; Edward T. Lentz

[57] ABSTRACT

A method for identifying new classes of chemical entities which dissociate specific protein-protein complexes. Antibodies are employed to specifically quantitate target protein-protein complexes.

16 Claims, 2 Drawing Sheets

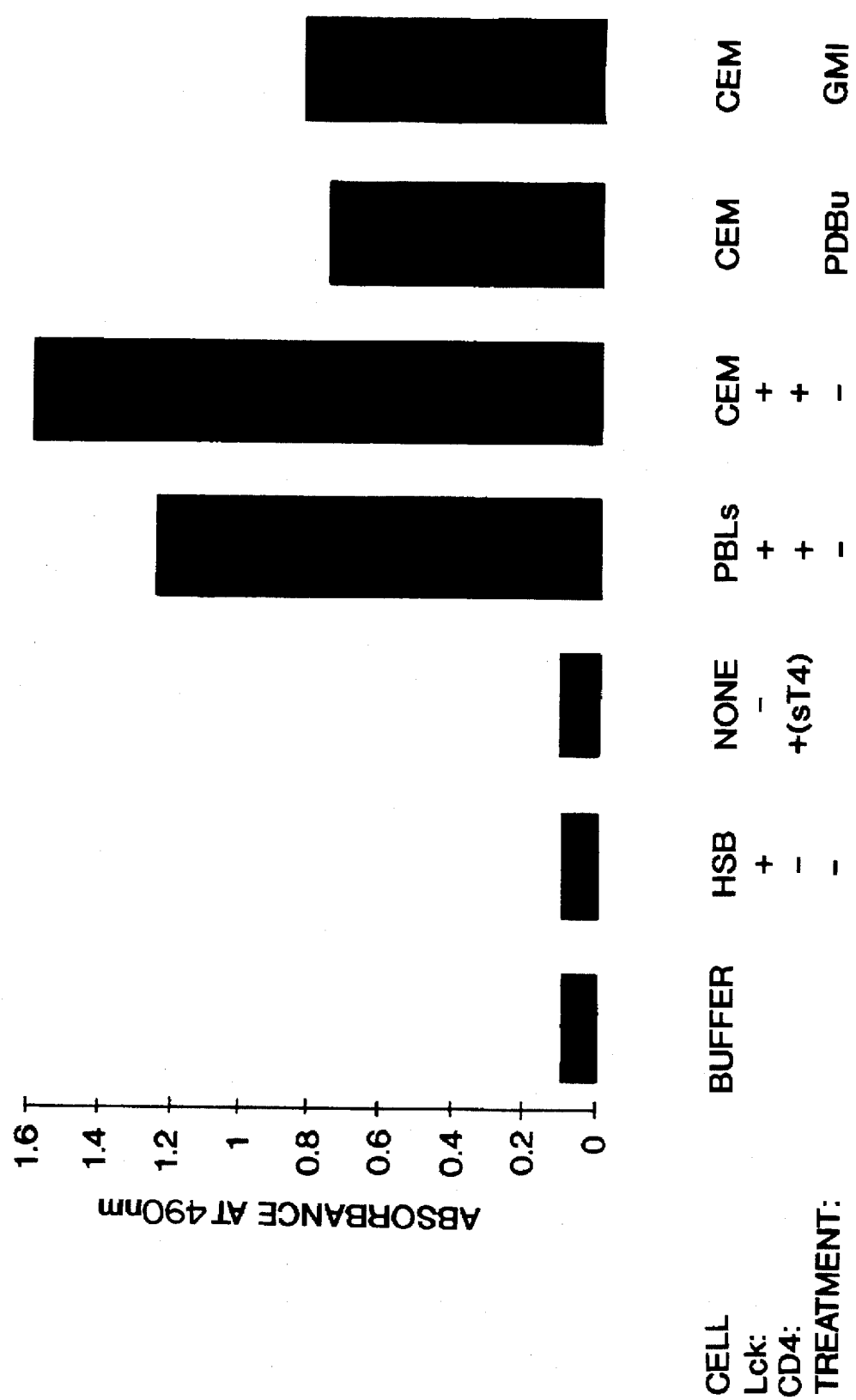
FIG. 2 PROPERTIES OF THE Lck/CD4 ELISA-LIKE ASSAY.

METHOD FOR SCREENING COMPOSITIONS

FIELD OF THE INVENTION

This invention relates to a method for screening compositions which interfere with any pathology resulting from biochemical signal transduction through protein-protein complexes. More specifically, this invention relates to methods for identifying agents which dissociate specific protein-protein complexes.

BACKGROUND OF THE INVENTION

It is known that protein-protein interactions are a key element in biochemical signal transduction. Interference with these interactions, when a part of a disease state, through agents which dissociate or inhibit the formation of specific protein complexes would be expected to have therapeutic effects on an organism.

Exemplary of the importance of biochemical signal transduction through specific protein-protein interactions is the T-lymphocyte-activation cascade. T lymphocytes predominantly recognize foreign antigen when associated with membrane-bound products of the major histocompatibility complex (MHC) on the surface of antigen-presenting cells. Molecular interactions between antigen/MHC complex and a T lymphocyte carrying an antigen-specific T-cell receptor (TcR) lead to T cell activation by initiating a series of programmed biochemical events culminating in the production of lymphokines, expression of either helper/inducer or cytotoxic/suppressor T cell function and clonal proliferation. See Weiss et al., *Ann. Rev. Immunol.* 4, 593–619 (1986) and Rudd et al., *Immunol. Rev.* 111, 225–266 (1989).

The T-cell surface molecules, CD4 and CD8, cooperate with the TcR/CD3 complex in the recognition of foreign antigen and contribute to a trimolecular recognition unit by interacting with nonpolymorphic regions of MHC class II and class I antigens, respectively. In the course of these interactions, CD4 and CD8 molecules transmit independent intracellular signals (Bierer et al., *Ann. Rev. Immunol.* 7, 579–599 (1989) and Bierer et al., *Immunol. Rev.* 111, 267–294 (1989)) and their resultant aggregation with the TcR/CD3 complex greatly enhances the proliferation of T cells (Eichmann et al., *Eur. J. Immunol.* 17, 643–650 (1987) and Anderson et al., *J. Immunol.* 139, 678–682 (1987)).

Monomeric CD4 and the two-subunit ($\alpha$ and $\beta$) CD8, members of the immunoglobulin superfamily, are transmembrane glycoproteins with short cytoplasmic domains. CD4 is expressed predominantly on T-helper/inducer lymphocytes, while CD8 is predominantly expressed on cytotoxic and suppressor T lymphocytes (Reinherz et al., *Immunol. Rev.* 81, 95–129 (1985) and Snow et al., *J. Biol. Chem.* 258, 14675–14681 (1983)).

CD4 and the $\alpha$ chain of CD8 heterodimer have been found to be physically associated through their cytoplasmic tails with a portion of the unique amino-terminal domain of the src-related, lymphocyte-specific protein tyrosine kinase, $p56^{lck}$ (Lck). See Rudd et al., *Proc. Natl. Acad. Sci. USA*, 85, 5190–5194 (1988) and Veillette et al., *Cell*, 55, 301–308 (1988). By analogy with receptor tyrosine kinases, the Lck/CD4 and Lck/CD8 complexes probably play an integral role in generating signals leading to T cell proliferation and differentiation. Additionally, a number of experimental approaches have suggested that the presence of Lck is essential for T cell activation. See Straus et al., *Cell*, 70, 585–593 (1992); Chan et al., *Ann. Rev. Immunol.* 12, 555–592 (1994); Molina et al., *Nature*, 357, 161–164 (1992); and Veillette et al., *Nature*, 338, 257–259 (1989).

In resting T lymphocytes, 50–60% of cellular Lck is associated with CD4. Genetic and mutational analysis studies have demonstrated that an intact pre-formed Lck/CD4 complex, which is found in MHC class II-restricted helper T lymphocytes, is essential for a functional response of these cells to foreign antigen. See Miceli et al., *Proc. Natl. Acad. Sci. USA*, 88, 2623–2627 (1991); Glaichenhaus et al., *Cell*, 64, 511–520 (1991); and Turner et al., *Cell*, 60, 755–765 (1990). Therefore, agents which selectively dissociate the CD4/Lck complex or those that inhibit complex formation would be expected to inhibit T-cell activation in vitro, leading to T-cell-specific immunosuppressive drugs. Such agents are expected to be useful in the treatment of autoimmune diseases and/or allograft rejection.

Although no direct evidence exists to support a pivotal role of the Lck/CD8 complex in the response of MHC class-I restricted T lymphocytes to antigen, it is believed that the CD8/Lck complex may play an integral role in generating signals leading to activation and proliferation of CD8-positive T lymphocytes. It is also believed that the CD8-positive cytotoxic T lymphocytes are responsible for generating organ toxicity in transplantations. Therefore, agents which selectively dissociate the Lck/CD8 complex or those that inhibit complex formation are expected to be useful for the treatment of allograft rejection.

Present techniques which measure the amount of CD4- or CD8-associated Lck rely on conventional, labor-intensive techniques involving immunoprecipitation such as detecting Lck in CD4 or CD8 immunoprecipitate by immune complex kinase assay using [$^{32}$p] radioisotopes or Western blotting techniques. These techniques require SDS-polyacrylamide gel electrophoresis and autoradiography. Thus, in order to discover protein—protein complex dissociating agents, such as those which dissociate CD4/Lck and CD8/Lck complexes, a need exists for a facile, high-throughput assay to measure specific target protein complexes.

SUMMARY OF THE INVENTION

Accordingly, one aspect of the present invention is a method for identifying compounds capable of dissociating a target protein complex comprising quantitating the target protein complex by an ELISA-based assay in the presence of and the absence of putative dissociative compounds.

Another aspect of the invention is a method for identifying compounds capable of dissociating a target protein complex comprising the steps of:

a) providing an identical first and second target protein complex;

b) contacting the first target protein complex with compositions comprising putative target protein complex dissociating compounds;

c) reacting the first and the second target protein complexes separately with a solid-phase first antibody specific for a first component of the target protein complex, to form a first and a second captured protein complex;

d) reacting the first and the second captured protein complexes separately with a second antibody specific for a second component of the target protein complex, to form a first and a second captured protein/second antibody complex; and e) quantitating the first and the second captured protein/second antibody complex, whereby a decreased amount of the first captured protein/second antibody complex relative to the second captured protein/second antibody complex indicates compounds which dissociate the target protein complex.

Yet another aspect of the invention is a method for identifying compounds capable of dissociating CD4/p56$^{lck}$ and CD8/p56$^{lck}$ T-cell receptor complexes.

BRIEF DESCRIPTION OF THE FIGURES

FIG. 2 illustrates the selectivity of the method of the invention for a target protein complex.

DETAILED DESCRIPTION OF THE INVENTION

Figure 1:
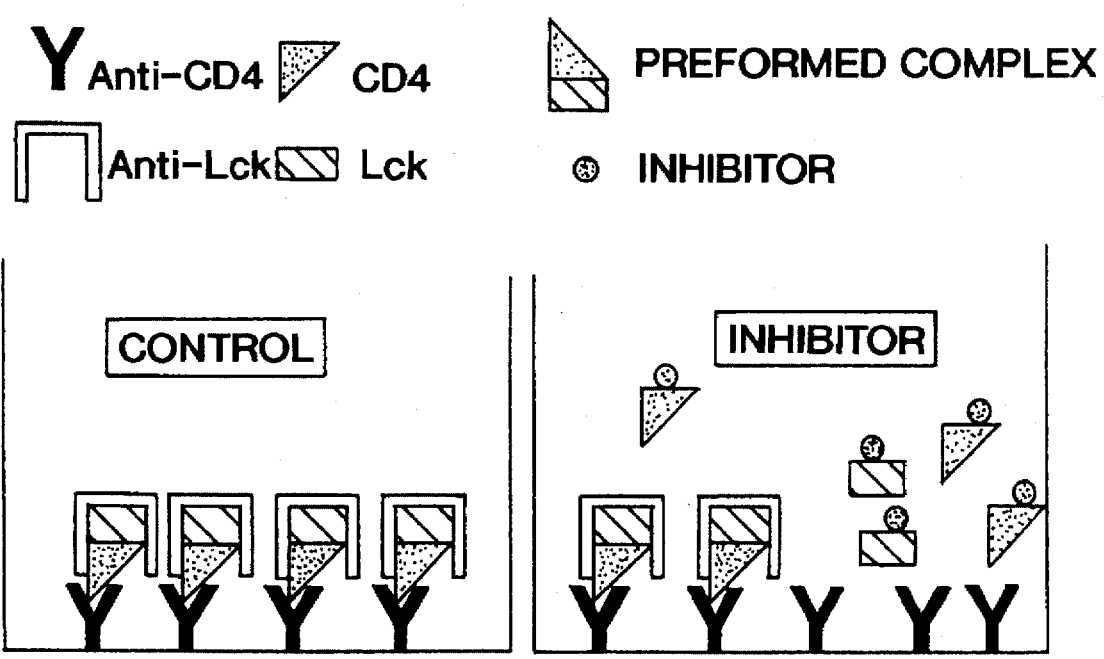
FIG. 1 schematically illustrates an embodiment of the invention.

An aspect of the present invention is a method for identifying compounds capable of dissociating a target protein complex. In general, a method for identifying compounds capable of dissociating a target protein complex comprising quantitating the target protein complex by an ELISA-based assay in the presence of and the absence of putative dissociative compounds is employed. By the method of the invention, compounds capable of dissociating a target protein complex are identified by a facile, high-throughput, specific, cell-free assay. The method of the invention is useful for drug discovery.

The target protein complex can be any protein complex where two or more proteins are associated noncovalently and dissociation and/or inhibition of the interaction of the complex components will have a therapeutic result. It will be recognized by those of skill in the art that any compounds which dissociate a target protein complex may also inhibit any reassociation and any initial association of the complex components. The target protein complexes may be of either intracellular or extracellular origin.

In one embodiment of the invention, identical first and second target protein complexes are provided by extracts of cells expressing the target protein complex or by recombinant techniques. Alternatively, intact cells associated with the first and the second target protein complexes provide the complexes. The first target protein complex is then contacted with compositions comprising putative target protein complex dissociating compounds.

Compositions which may be screened as target protein complex dissociating compounds include a variety of organic molecules, separately or in combination, or mixtures of organic molecules such as natural product extracts, soil extracts and fermentation broths. Methods to provide the first and second target protein complexes such as cell extract preparation protocols and recombinant techniques such as cloning and expression of the structural genes encoding the components of the target protein complex or gene fragments encoding the binding regions in heterologous systems are well known in the art. Whole cell culture techniques to provide intact cells are also well known in the art. Cell extracts are prepared after contact of the intact cells with the putative dissociating compounds.

The first and the second target protein complexes are separately reacted with a solid-phase first antibody specific for a first component of the target protein complex. The first antibody can be a monoclonal, polyclonal or an isolated IgG. Preferably, the first antibody has a high affinity for the first component of the target protein complex. Most preferably, the first antibody is a monoclonal. The antibody is attached to a solid substrate, preferably by adsorption to a microtiter plate well. Reaction of the first antibody with the first component of the target protein complex removes the soluble target protein complex from solution forming a first and a second solid-phase captured protein complex.

The first and the second captured protein complex are reacted separately with a second antibody specific for a second component of the target protein complex. The second antibody can be a monoclonal, polyclonal or an isolated IgG. Preferably, the second antibody has a high affinity for the second component of the target protein complex. Most preferably, the second antibody is an isolated IgG. Reaction of the second antibody with the second component of the target protein complex forms a solid-phase captured protein/second antibody complex.

The amount of the captured first and second protein/second antibody complexes is quantitated. A decreased amount of the first captured protein/second antibody complex relative to the second captured protein/second antibody complex is indicative of compounds which dissociate the target protein complex.

Quantitation of the first and second captured protein/second antibody complexes is by an enzyme-linked immunosorbent-based assay (ELISA-based) employing a tertiary antibody reactant covalently coupled to an enzyme or biotin. The tertiary antibody reacts with the second antibody, unbound conjugate is washed out and a chromogenic or fluorogenic substrate is added. As the substrate is hydrolyzed by the bound enzyme conjugate, a colored or fluorescent reporter molecule product is generated. The amount of reporter product generated is proportional to the amount of target protein complex present in the test mixture.

Exemplary is an ELISA-based assay where, for example, the second antibody is of rabbit origin and a tertiary horseradish peroxidase-conjugated goat anti-rabbit IgG (HRP-GARIG) is reacted with the captured protein/second antibody complex. Complexed HRP-GARIG is detected through reduction of the chromogenic peroxidase substrate, o-phenylenediamine dihydrochloride. Other detection techniques include biotin-streptavidin, alkaline phosphatase, β-galactosidase, glucoamylase and urease.

Test compounds which dissociate the target protein complex are identified by a decreased reporter molecule signal relative to controls lacking test compound. Once identified as causing dissociation of the target protein complex by the method of the invention, the potential dissociative agents can then be tested in secondary screens to establish their efficacy on intact cells directly. If mixtures, such as natural product extracts, are tested, it may be desirable to subject the mixture to chemical and/or physical separation techniques well-known in the art to isolate the active compound from the mixture. It may also be desirable to use the method of the invention as a bioassay to monitor the presence of the compound of interest during any purification process.

An exemplary target protein complex is the CD4/Lck complex present in helper T lymphocytes, an essential component in the T-cell activation cascade. Selective CD4/Lck complex dissociation agents identified through the method of the invention will provide lead compounds for development of selective immunosuppressive and allograft rejection therapeutics.

First and second CD4/p56$^{lck}$ complexes are provided by intact T lymphocytes, T-lymphocyte cell extracts or are produced recombinantly. Preferably, if intact cells or cell extracts are used, they are provided from CEM cells, an acute lymphoblastic CD4-positive human T-cell line. Also preferred is the CD4-positive, CD8-positive thymocytic T-cell line, SupT1.

The first provided CD4/p56$^{lck}$ complex is contacted with compositions comprising CD4/p56$^{lck}$ complex dissociating compounds. Subsequently, the first and the second CD4/ p56$^{lck}$ complexes are reacted with a CD4 antibody attached to a solid substrate to form a captured CD4/p56$^{lck}$ complex. When intact cells are used, cell extracts are prepared after contact of the cells with the putative dissociating compounds. Preferably, the CD4 antibody is a monoclonal antibody, such as OKT4. Other CD4 monoclonal antibodies may also be used in the method of the invention. The captured CD4/p56$^{lck}$ complex is reacted with a p56$^{lck}$ antibody to form a captured CD4/p56$^{lck}$/p56$^{lck}$ antibody complex. Preferably, the p56$^{lck}$ antibody is anti-p56$^{lck}$ IgG raised against a portion of the amino or carboxy terminal of p56$^{lck}$. Most preferably, the p56$^{lck}$ antibody is raised against a portion of the carboxy terminal of p56$^{lck}$.

The presence of the captured CD4/p56$^{lck}$/p56$^{lck}$ antibody complex is detected by an ELISA-based assay as described above. Compounds which dissociate the CD4/p56$^{lck}$ complex are identified by a decrease in reporter product relative to controls.

Another exemplary target protein complex is the CD8/Lck complex present in some T-lymphocyte subsets. Selective CD8/Lck complex dissociation agents identified through the method of the invention will provide lead compounds for development of therapeutics for allograft rejection. Substitution of a CD8 antibody in the above-described method for CD4/Lck, preferably a monoclonal antibody, allows selective and accurate measurement of CD8/Lck complex and identification of complex dissociative agents.

The method of the invention is selective for the target protein complex and does not detect unassociated components of the complex. In the CD4/Lck embodiment, the method of the invention can detect complex in extracts from as few as 10,000 T cells and is linear up to $6.0\times10^5$ cell equivalents per well, when cultured CD4-positive/Lck-positive T cell lines such as CEM and SupT1 are used. Also, changes as small as 10% in the amount of complex can be detected. In the CD8/Lck embodiment, the method of the invention can detect complex in extracts from as few as 40,000 cells and is linear up to $1.25\times10^6$ cell equivalents per well, when cultured Lck-positive/CD8-positive T cell lines such as SupT1 are used. In both the CD4/Lck and CD8/Lck embodiments, the method of the invention can detect CD4/Lck and CD8/Lck complexes in extracts from freshly prepared human peripheral blood lymphocytes using plates coated with CD4 and CD8 monoclonal antibodies, respectively.

The present invention will now be described with reference to the following specific, non-limiting examples.

EXAMPLES

CD4/Lck Dissociation Assay

Acute lymphoblastic CD4-positive human T-cells, from the T-cell line CEM (ATCC CCL 119), were grown in suspension in RPMI-1640 medium supplemented with 10% heat-inactivated fetal calf serum at 37° C. to a cell density of $0.8-1.2\times10^6$ cells/ml. Detergent extracts of CEM cells were prepared by pelleting cells, washing with Dulbecco's phosphate buffered saline without Ca and Mg (D-PBS) at 4° C. and resuspending the cell pellet in sufficient freshly prepared extraction buffer (50 mM Tris, pH 8.0, 150 mM NaCl, 2 mM EDTA, 50 mM NaF, 3% NONIDET™ P-40, 0.1 mM Na vanadate, 0.1 mM PMSF, 10 ug/ml leupeptin, 10 ug/ml aprotinin, 10 ug/ml TLCK) to yield $1.0\times10^8$ cells in a volume of 1 ml. The cell pellet was resuspended gently on ice until a homogeneous suspension was obtained and kept on ice for at least 30 min with occasional vortexing. The suspension was then centrifuged at 29,000 xg for 30 min at 4° C.; the clear cell extract supernatant was transferred to a clean tube and placed on ice.

Cell extracts were diluted 16-fold with ice-cold PBS (0.1M phosphate, 0.15M NaCl, ph 7.4) containing 0.5% (w/v) BSA and 0.05% (v/v) TWEEN™ 20 (PBT) to yield $6.25\times10^6$ cell equivalents/ml. Candidate dissociative agents were diluted to 1 mg/ml with ddH$_2$O and 10 ul were added to Corning plate wells. A 90 ul volume of diluted cell extract ($5.6\times10^5$ cell equivalents) were added to the Corning plate wells containing an organic solvent to provide a final candidate agent concentration of 0.1 mg/ml. Exemplary organic solvents are DMSO and ethanol. The resulting final concentration of organic solvent was 1%. The plates were incubated for 30 min at 30° C. in a water bath and then transferred to ice. Alternatively, diluted cell extracts can be incubated with candidate agents for 2 to 3 hours at room temperature (22°–25° C.).

ELISA assay plate wells were prepared by coating MaxiSorp™ (Nunc, round-bottom wells) or TITERTEK™ plate wells overnight at 4° C. with 100 ul of 2.5 ug/ml OKT4 CD4 mAb in 0.1M NaHCO$_3$, pH 9.2. TITERTEK™ and Corning ELISA plates were also successfully used. Other CD4 monoclonal antibodies which bind to portions of the V1 domain in the extracellular portion of the CD4 molecule may also be used. All CD4 monoclonal antibodies were either purchased from Ortho or purified from specific hybridomas available from the ATCC. OKT4 hybridoma is available under ATCC CRL 8002.

When ready for use, the coating solution was removed and the wells rinsed 3× with PBS. A blocking step was performed by adding 0.3 ml PBT per well and incubating at least 30 min at 37° C. All PBT was removed and 50 ul of diluted cell extracts were added to the test wells. 50 ul of extraction buffer/PBT (1:15, v/v) were added to the assay blank wells. The plates were sealed and incubated 1 hour at 4° C.

Carboxy-Lck Ab (C-Lck) was generated in rabbit against a peptide corresponding to the last 30 residues of the Lck molecule. Commercial (Upstate Biotechnology Inc., Cat. No. 06-135) and in-house prepartions of the C-Lck were used. The IgG fraction of the C-Lck antiserum was purified and stored at −70° C. as a 1 mg/ml solution in D-PBS. Portions were diluted 300-fold with ice-cold PBT and used within 1 week. 50 ul of diluted C-Lck were added to each well; the plates were sealed and incubated 1 hour at 4° C. The plates were washed 3× with PBS and 0.1 ml of horseradish peroxidase-goat-anti-rabbit IgG (HRP-GARIG, Pierce Cat. No. 31462), diluted 1:8000 in ice-cold PBT, was added to the wells. The plates were sealed and incubated 30 min at 4° C. HRP substrate/chromogen solution was prepared fresh for each plate by dissolving 10 mg o-phenylenediamine dihydrochloride (OPD, Sigma Cat. No. P-8287) in 24 ml citrate-phosphate buffer (0.1M Na$_2$HPO$_4$·12 H$_2$O adjusted to pH 5.0 with 0.1M citric acid) in a brown bottle and then adding 8 ul of 30% H$_2$O$_2$. The plates were incubated 5–15 min at room temperature in the dark until a yellow color was observed. The color development was stopped with 50 ul of 4.5M H$_2$SO$_4$ and the color read at 490 nm.

Exemplary screening results are shown in Table 1. The results are reported as IC50 (uM), i.e., the concentration of test compound which dissociated 50% of the target CD4/Lck protein complex relative to controls.

TABLE 1

| COMPOUND | IC$_{50}$ (μM) |
| --- | --- |
| Genistein | >200 |
| LC-A23 | >500 |
| LC-A46 | 300 |
| Crambine A | <100 |
| Halitoxin | <100 |

Genistein is the compound 5,7-dihydroxy-4'-methoxyisoflavone. LC-A23 and LC-A26 are the tyrphostin compounds, 2-cyano, 3-(3,4-dihydroxyphenyl)acrylonitrile and trans-2-cyano, 3-(3,4-dihydroxyphenyl)acrylamide, respectively. Crambine A is a guanidine alkaloid isolated from the Mediterranean sponge *Crambe crambe* (*Tetrahedron Letters* 31, 6531-6534 (1990)). Halitoxin is a crude mixture containing pyridinium compounds extracted from a marine organism.

The selectivity and sensitivity of the assay are shown in FIG. 2. Extracts were prepared from 3 cell types. The HSB T-cell line (ATCC CCL 120.1) is Lck-positive/CD4-negative. Peripheral blood lymphocytes (PBL) were isolated from blood donated by local volunteers; these preparations are typically positive for Lck, CD4 and CD8. The CEM T-cell line is Lck-positive/CD4-positive. The expression of Lck and CD4 is indicated with "+" or "−" under the graph bars. In the absence of a cell line which was CD4 and Lck negative, preparations of recombinant soluble CD4 (sT4) were used. CEM cells were treated with 50 nM phorbol dibutyrate (PDBu) or 100 uM of the ganglioside GM1, agents which dissociate the CD4/Lck complex, at 37° C. for 15 and 30 minutes, respectively. PDBu activates protein kinase C leading to dissociation of Lck from CD4 and subsequent down regulation of CD4. GM1 is a glycososphingolipid ganglioside which binds to regions in the CD4 extracellular domain and has been show to dissociate Lck from CD4. Control preparations of PBL, HSB and CEM cells were not treated. Both treated and control cell preparations were extracted at 1×10$^8$ cells/ml. Extracts were diluted 8-fold with PBT and 50 ul of diluted extract (6×10$^5$ cells) or 50 ul of 0.2 mg/ml sT4 were applied per well of Maxisorp™ plates that were coated with 250 ng of OKT4.

The first five result bars presented in FIG. 2 demonstrate that a signal is generated in the assay only when there is a cellular source containing both CD4 and Lck, i.e., a CD4/Lck complex. The assay does not detect free Lck or free CD4. Thus, HSB cells which contained Lck but did not contain CD4 did not produce a signal in the assay. When sT4 was used, no signal was generated due to lack of a CD4/Lck complex. PBL and CEM cells both express Lck and CD4; these two cell types are shown in FIG. 2 to generate a signal in the assay which is 12 to 15-fold over background (buffer).

The last three result bars of FIG. 2 demonstrate that treatments which were shown to dissociate the CD4/Lck complex result in a reduction of the signal generated in the assay. Thus, when CEM cells were treated with PDBu, a 60% reduction in generated signal was observed. This result correlates well with published results obtained by conventional detection assays. Additionally, the ability of GM1 to dissociate Lck from CD4 was confirmed with the present assay.

Other results obtained with the present assay demonstrated that no signal was generated from extracts of CEM cells when antibodies against the src family members p59$^{fyn}$ and p56$^{lyn}$ were used for complex detection in place of Lck antibody. Further, the assay did not detect CD8/Lck complex in extracts from CD8-positive/Lck-positive T cells.

Alternatively, CEM cells are grown as above and resuspended in serum-free medium to a cell density of 5×10$^6$ cells/ml. Candidate dissociative agents are diluted to 1 mg/ml with ddH$_2$O and 10 ul are added to Corning plate wells. A 90 ul volume of diluted intact cells (4.5×10$^5$ cells) are added to the Corning plate wells containing an organic solvent to provide a final candidate agent concentration of 0.1 mg/ml as described above. The cells are incubated with the agents for 30 min at 37° C. The plates are centrifuged and the cell pellet is extracted with 0.1 ml of extraction buffer as described above. The microtiter plates are centrifuged and 50 ul of extract (2.25×10$^5$ cell equivalents) are applied to coated and blocked ELISA plates as described above. The results obtained would be similar to those described above.

A CD8/Lck complex was selectively and accurately measured in SupT1 (ATCC CRL 1942) extracts by substituting a CD8 monoclonal antibody (OKT8) purified from a hybridoma (ATCC CRL 8014) into the coating step of the assay described above. Free CD8 and free Lck were not detected. No signal was detectable when antibodies against the src family members p59$^{fyn}$ and p56$^{lyn}$ were used for complex detection in place of Lck antibody. Further, the assay did not detect CD4/Lck complex in extracts from CD4-positive/Lck-positive T cells.

The present invention may be embodied in other specific forms without departing from the spirit or essential attributes thereof, and, accordingly, reference should be made to the appended claims, rather than to the foregoing specification, as indicating the scope of the invention.

I claim:

1. A method for identifying compounds capable of dissociating T-cell receptor complexes formed between CD4 and p56$^{lck}$ comprising the steps of:

a) providing an identical first and second CD4/p56$^{lck}$ complex;

b) contacting the first CD4/p56$^{lck}$ complex with compositions comprising putative CD4/p56$^{lck}$ complex dissociating compounds;

c) reacting the first and the second CD4/p56$^{lck}$ complexes separately with a solid-phase CD4 antibody to form a first and a second captured CD4/p56$^{lck}$ complex;

d) reacting the first and the second captured CD4/p56$^{lck}$ complex with a p56$^{lck}$ antibody to form a first and a second captured CD4/p56$^{lck}$/p56$^{lck}$ antibody complex; and e) quantitating the first and the second captured CD4/p56$^{lck}$/p56$^{lck}$ antibody complex, whereby a decreased amount of the first captured CD4/p56$^{lck}$/second antibody complex relative to the second captured CD4/p56$^{lck}$/second antibody complex indicates compounds which dissociate the complex formed between CD4 and p56$^{lck}$.

2. The method of claim 1 wherein the first and the second CD4/p56$^{lck}$ complexes are provided by CEM cell extracts.

3. The method of claim 1 wherein the first and the second CD4/p56$^{lck}$ complexes are provided by intact CEM cells.

4. The method of claim 1 further comprising the step of:

b)1) extracting said T-cell receptor complexes from the intact cells.

5. The method of claim 1 wherein the CD4 antibody is a monoclonal antibody.

6. The method of claim 5 wherein the monoclonal antibody is OKT4.

7. The method of claim 1 wherein the p56$^{lck}$ antibody is anti-p56$^{lck}$ IgG.

8. The method of claim 7 wherein the anti-p56$^{lck}$ IgG is raised against the carboxy terminal of p56$^{lck}$.

9. A method for identifying compounds capable of dissociating T-cell receptor complexes formed between CD8 and p56$^{lck}$ comprising the steps of:

a) providing an identical first and second CD8/p56$^{lck}$ complex;

b) contacting the first CD8/p56$^{lck}$ complex with compositions comprising putative CD8/p56$^{lck}$ complex dissociating compounds;

c) reacting the first and the second CD8/p56$^{lck}$ complexes separately with a solid-phase CD8 antibody to form a first and a second captured CD8/p56$^{lck}$ complex;

d) reacting the first and the second captured CD8/p56$^{lck}$ complex with a p56$^{lck}$ antibody to form a first and a second captured CD8/p56$^{lck}$/p56$^{lck}$ antibody complex; and e) quantitating the first and the second captured CD8/p56$^{lck}$/p56$^{lck}$ antibody complex, whereby a decreased amount of the first captured CD8/p56$^{lck}$/second antibody complex relative to the second captured CD8/p56$^{lck}$/second antibody complex indicates compounds which dissociate the complex formed between CD8 and p56$^{lck}$.

10. The method of claim 9 wherein the first and the second CD8/p56$^{lck}$ complexes are provided by SupT1 cell extracts.

11. The method of claim 9 wherein the first and the second CD8/p56$^{lck}$ complexes are provided by intact SupT1 cells.

12. The method of claim 11 further comprising the step of:

b)1) extracting said T-cell receptor complexes from the intact cells.

13. The method of claim 9 wherein the CD8 antibody is a monoclonal antibody.

14. The method of claim 13 wherein the monoclonal antibody is OKT8.

15. The method of claim 9 wherein the p56$^{lck}$ antibody is anti-p56$^{lck}$ IgG.

16. The method of claim 15 wherein the anti-p56$^{lck}$ IgG is raised against the carboxy terminal of p56$^{lck}$.

* * * * *